United States Patent
Dubois et al.

(10) Patent No.: US 10,959,638 B2
(45) Date of Patent: Mar. 30, 2021

(54) CONDUCTION VELOCITY AND PATTERN MAPPING

(71) Applicant: CARDIOINSIGHT TECHNOLOGIES, INC., Independence, OH (US)

(72) Inventors: Rémi Dubois, Bordeaux (FR); Corentin Dallet, Bordeaux (FR)

(73) Assignee: CARDIOINSIGHT TECHNOLOGIES, INC., Independence, OH (US)

(*) Notice: Subject to any disclaimer, the term of this patent is extended or adjusted under 35 U.S.C. 154(b) by 100 days.

(21) Appl. No.: 15/975,572

(22) Filed: May 9, 2018

(65) Prior Publication Data
US 2018/0325400 A1    Nov. 15, 2018

Related U.S. Application Data

(60) Provisional application No. 62/503,747, filed on May 9, 2017.

(51) Int. Cl.

| | | |
|---|---|---|
| *A61B 5/044* | (2006.01) |
| *A61B 5/04* | (2006.01) |
| *A61B 5/042* | (2006.01) |
| *A61B 5/0464* | (2006.01) |
| *A61B 5/0452* | (2006.01) |
| *A61B 18/14* | (2006.01) |
| *A61B 90/00* | (2016.01) |

(Continued)

(52) U.S. Cl.
CPC ............ *A61B 5/044* (2013.01); *A61B 5/0452* (2013.01); *A61B 5/0464* (2013.01); *A61B 18/1492* (2013.01); *A61B 34/25* (2016.02); *A61B 90/37* (2016.02); *A61B 18/02* (2013.01); *A61B 18/12* (2013.01); *A61B 18/14* (2013.01); *A61B 2018/00351* (2013.01); *A61B 2018/00577* (2013.01); *A61B 2018/00791* (2013.01); *A61B 2018/00839* (2013.01); *A61B 2018/0212* (2013.01); *A61B 2090/376* (2016.02); *A61N 1/056* (2013.01); *A61N 1/0587* (2013.01); *A61N 7/02* (2013.01)

(58) Field of Classification Search
CPC ........... A61B 8/08; A61B 8/485; A61B 8/488; A61B 8/0883; A61B 8/5276; A61B 8/543; G01S 15/00; G01S 15/89; G01S 15/8979; Y10S 128/916
USPC ........................................................ 600/449
See application file for complete search history.

(56) References Cited

U.S. PATENT DOCUMENTS

| | | | |
|---|---|---|---|
| 10,285,611 B1* | 5/2019 | Harley | ............... A61B 5/04012 |
| 2003/0158483 A1* | 8/2003 | Jackson | ................. A61B 8/485 |
| | | | 600/449 |

(Continued)

FOREIGN PATENT DOCUMENTS

WO    2015/134237 A1    9/2015

OTHER PUBLICATIONS

Applicant: Cardioinsight Technologies, Inc.; International Search Report and Written Opinion; Authorized Officer: Yeonkyung Kim; Date of Completion: Oct. 24, 2018; 10 pgs.

*Primary Examiner* — Jon Eric S Morales
(74) *Attorney, Agent, or Firm* — Tarolli, Sundheim, Covell & Tummnio LLP

(57) ABSTRACT

Systems and methods can be used to determine conduction velocity and generate one or more conduction velocity and/or pattern maps to facilitate identification of arrhythmogenic mechanisms.

26 Claims, 13 Drawing Sheets

(51) Int. Cl.
*A61B 34/00* (2016.01)
*A61B 18/00* (2006.01)
*A61N 1/05* (2006.01)
*A61B 18/02* (2006.01)
*A61N 7/02* (2006.01)
*A61B 18/12* (2006.01)

(56) References Cited

U.S. PATENT DOCUMENTS

| | | |
|---|---|---|
| 2011/0137171 A1 | 6/2011 | Lee et al. |
| 2015/0216438 A1 | 8/2015 | Bokan et al. |
| 2016/0045133 A1* | 2/2016 | Balachandran .... A61B 18/1492 600/509 |
| 2016/0100770 A1 | 4/2016 | Afonso et al. |
| 2017/0014086 A1 | 1/2017 | Li et al. |

* cited by examiner

CONDUCTION VELOCITY AND PATTERN MAPPING

CROSS-REFERENCE TO RELATED APPLICATION

This application claims the benefit of priority from U.S. Provisional Patent Application No. 62/503,747, filed May 9, 2017 and entitled CONDUCTION VELOCITY AND PATTERN MAPPING, which is incorporated herein by reference in its entirety.

TECHNICAL FIELD

This disclosure relates to conduction velocity mapping and pattern mapping.

BACKGROUND

Ventricular (VT) and atrial tachycardias (AT) are some of the most common clinical cardiac tachyarrhythmias. They are characterized by abnormal and fast muscular activity, with an organized electrical activity resulting from altered electrical propagation. Atrial tachycardia (AT) management is challenging due to mechanism complexity and altered electrogram (EGM) voltages, especially after AF ablation. However, post AF ablated ATs are still poorly investigated through electrocardiographic imaging (ECGI) that is currently used in clinics for noninvasive electro-anatomic mapping (EAM) of atrial arrhythmias.

SUMMARY

This disclosure relates to conduction velocity mapping and pattern mapping.

As one example, a method includes defining a region of interest around a given node on a three-dimensional surface of interest. Electrophysiological signals are stored, in memory, for each of a plurality of nodes distributed across the surface of interest. The method also includes orthogonally projecting the region of interest for the given node from the surface of interest onto a two-dimensional surface tangential to the given node. The method also includes. The method also includes estimating a two-dimensional conduction velocity vector for the given node based on analysis of the electrophysiological signal for the given node relative to other nodes in the region of interest. The method also includes estimating a three-dimensional conduction velocity vector for the given node based on the two-dimensional conduction velocity vector. In another example, one or more non-transitory computer readable media can be programmed with instructions which when executed by one or more processor perform such method.

As yet another example, a system may include memory to store machine readable instructions and data, the data including electrical data representing electrophysiological signals for a plurality of nodes distributed across a three-dimensional surface of interest. One or more processors may access the memory and execute the instructions. The instructions are programmed to determine a region of interest around a given node of the plurality of nodes on the surface of interest. The instructions are further programmed to project the region of interest around the given node from the surface of interest onto a two-dimensional surface tangential to the given node. The instructions are further programmed to estimate a two-dimensional conduction velocity vector for the given node based on analysis of the electrophysiological signal for the given node relative to other nodes in the region of interest. The instructions are further programmed to estimate a three-dimensional conduction velocity vector for the given node on the three-dimensional surface of interest based on the two-dimensional conduction velocity vector.

DETAILED DESCRIPTION

This disclosure provides a noninvasive diagnostic tool that helps to identify arrhythmogenic mechanisms, including atrial tachycardia (AT) and ventricular tachycardia (VT) mechanisms, using conduction velocity and/or associated electrical propagation pattern features. For example, conduction velocity and/or propagation pattern features across a three-dimensional (3D) region of interest (ROI) are determined and displayed in a graphical user interface (GUI), such as an electroanatomic map of a cardiac envelope (e.g., displaying patterns across a hear surface, such as an epicardial surface).

Clinical accuracy of the propagation mapping, the rotation and dispersion features across the 3D ROI using mathematical operators for noninvasive diagnosis of complex ATs and VTs may be improved, such as by displaying one or more graphical maps of 3D conduction velocity (CV) and/or rhythm patterns derived from the CV map. For example, such 3D CV and/or rhythm pattern maps may provide additional information across the 3D ROI that can visualize the effects of treatment (e.g., before and after ablation at one or more sites) and further identify one or more other treatment delivery sites to be targeted subsequently. As a result of the systems and methods disclosed herein, treatment (e.g., ablation) procedural time can be reduced and the overall procedure simplified. The approach herein also affords online use, such as in clinics. Additionally, the results pattern maps can be utilized for detection of specific AT or VT propagation pattern features (e.g., rotor and foci) for automated or semi-automated diagnosis.

Figure 1:
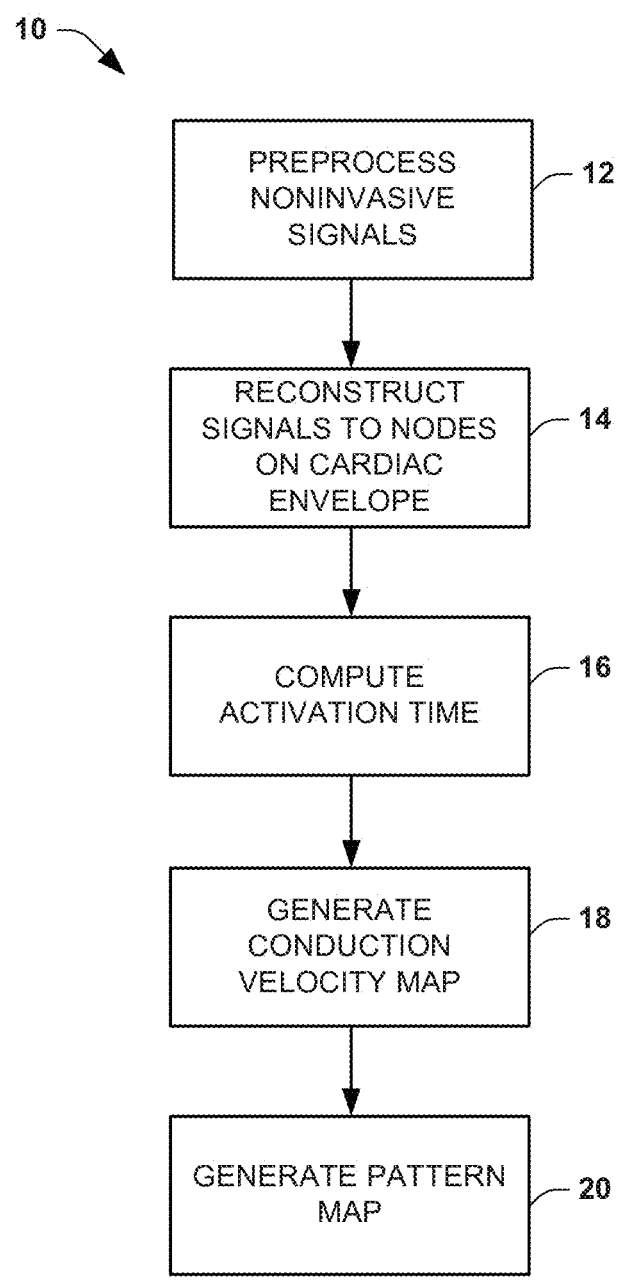
FIG. 1 is a flow diagram depicting an example of a method for generating conduction velocity maps and pattern maps.
Figure 2:
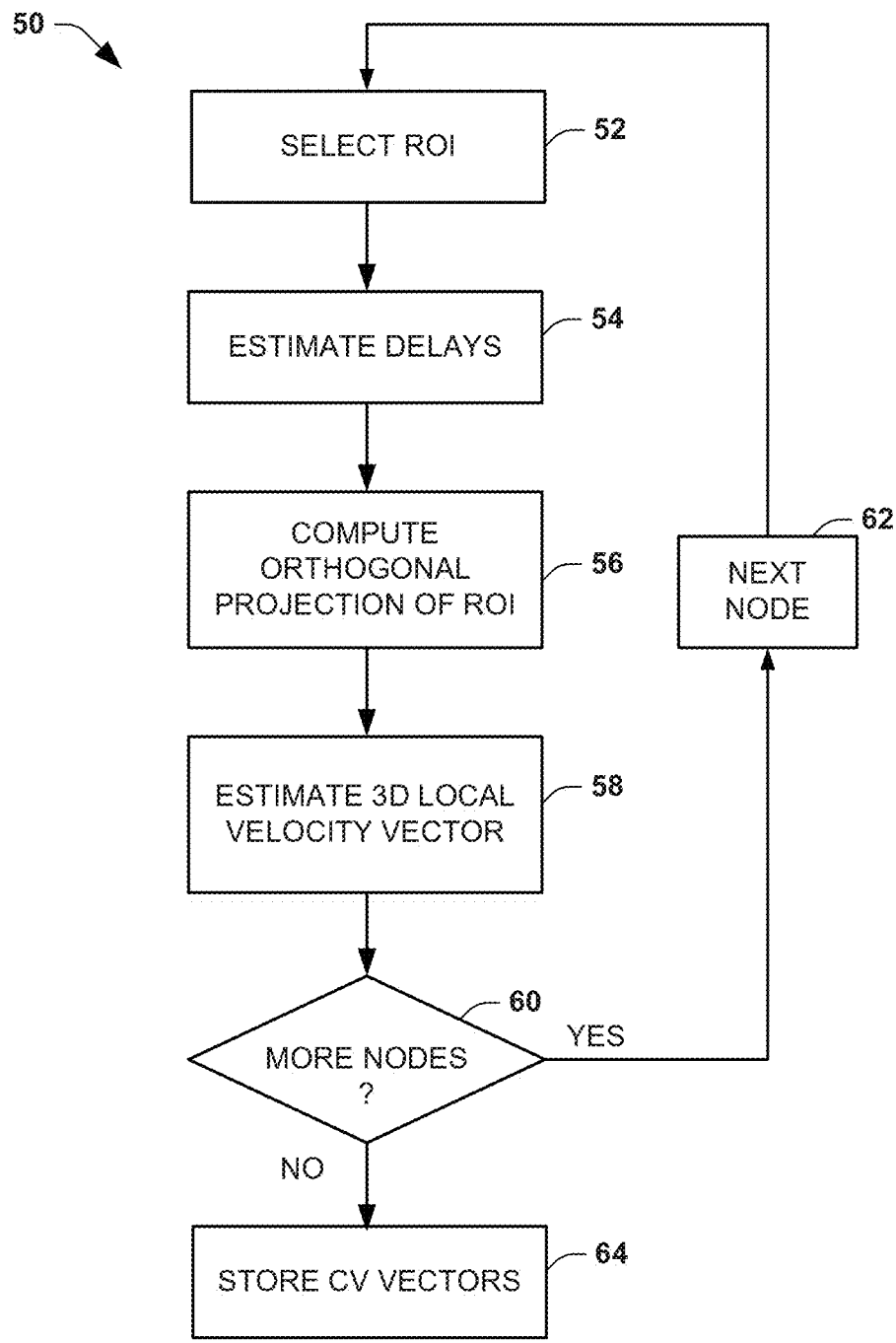
FIG. 2 is a flow diagram depicting an example method for performing conduction velocity mapping.
Figure 3:
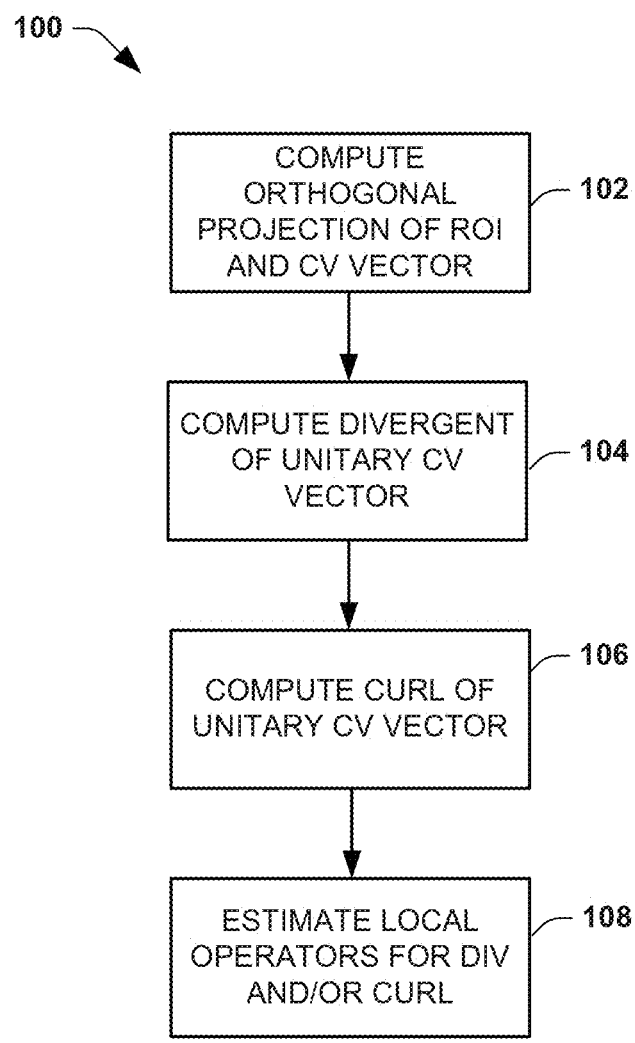
FIG. 3 is a flow diagram depicting an example method for performing pattern feature mapping.

In the flow diagrams disclosed herein FIGS. 1-3, for purposes of simplicity of explanation, the methods are shown and described as executing serially; however, it is to be understood and appreciated that such method is not limited by the illustrated order, as some aspects could, in other embodiments, occur in different orders and/or concurrently with other aspects from that shown and described herein. Moreover, not all illustrated features may be required to implement a method. Each method or relevant portions thereof can be implemented as instructions (e.g., code) stored in one or more non-transitory storage media as well as be executed by a processing resource (e.g., one or more processor cores) of a computer system, for example.

FIG. 1 is a flow diagram depicting an example high-level workflow corresponding to a method 10 for generating conduction velocity maps and pattern maps. This and other methods disclosed herein are useful to provide additional information not explicit in existing maps like activation maps. For example, a conduction velocity map or pattern map generated according to this disclosure provide electrophysiological information about the myocardium substrate to describe tissue properties and/or to identify arrhythmogenic mechanisms, such as reentrant circuits, anchor points for rotors or slow conducting areas. A further benefit from such maps is that they are computed over space (e.g., over a region of interest), operating as a kind of spatial filtering. As a result, users can better understand such mechanisms over the surface based on the electrical signals obtained for the surface over time.

The method begins at 12 to include preprocessing of electrical signals. The signals represent electrical activity measured across a surface of a patient's body over one or more time intervals. For example, a plurality of electrodes can be positioned on the patient's body to measure electrical activity (unipolar electrograms) across the body surface. The electrodes thus can measure the electrical signals non-invasively and the signals can stored as electrical data in memory for the preprocessing. As an example, the preprocessing at 12 may include one or more of the following:

a. QRS removal;
b. Template matching on the beats;
c. Computation of a unique reference ECG signal;
d. Determining beat location
e. Selecting one or more heart beats;
f. Waveform analysis (correlation coefficient);
g. Amplitude analysis (root mean square error); and
h. Computation of the averaged beat on each channel (lead) from the selection.

At 14, the method includes reconstructing the preprocessed signals to nodes on a cardiac envelope based on electrical data and geometry data (e.g., provided at 12). For example, the cardiac envelope is three-dimensional (3D) surface model that defines a mesh surface of a cardiac envelope (e.g., an epicardial surface). The mesh may be described by geometry data (stored in memory), such as includes a collection of nodes (vertices) that define a plurality of polygons (triangle or other polygons) forming the surface. Each polygon can include three or more vertices, such that adjacent vertices define edges that surround a face of each respective polygon. Therefore, at 14, corresponding electrogram signals are computed for each of the nodes on the surface based on the preprocessed signals derived from the body surface electrical signal measurements and geometry data.

As one example the reconstruction of signals on to the cardiac envelope may include solving the inverse problem (e.g., using the Method of Fundamental Solutions or other approach) to reconstruct unipolar epicardial electrograms on the cardiac envelope (epicardial surface) based on geometry data. For instance the geometry data includes patient atrium and torso 3D meshes (complex atrium geometry, location, orientation and size). The resulting geometry (3D spatial coordinates) and electrical data (reconstructed electrograms) are stored in memory. Examples of methods to compute reconstructed electrograms from measured body surface electrical signals are disclosed in U.S. Pat. Nos. 6,772,004 and 7,983,743, which are incorporated herein by reference. The reconstructed electrical signals across the mesh surface may be stored in memory as electroanatomical data, including electrical data representing the time-varying electrical potential (e.g., unipolar electrograms) estimated for each of the nodes over one or more time intervals and geometry data described nodes across the surface.

At 16, activation time is computed based on the reconstructed electrical signals on the surface envelope. For example, each node n of the mesh is defined by its 3-D Cartesian coordinates (x, y, z) and its activation time is computed based on the reconstructed electrical signals computed at 14. The activation time may be computed for the nodes distributed across one or more regions of interest on the surface, which may be for any sized area up to the entire surface envelope. For example, the activation time is computed from a method using the reconstructed electrograms and delays between neighboring nodes on the mesh, such as disclosed in U.S. Pat. No. 9,610,023, which is incorporated herein by reference.

At 18, a conduction velocity map is generated. The conduction velocity map is generated by computing a velocity vector based on the computed activation time for nodes distributed across one or more regions of interest, such as any sized area up to the entire surface (of the heart). For example, the conduction velocity vector may be estimated for each of the nodes based on spatial and temporal criteria derived from a set of neighboring nodes within a region of interest. As an example, the neighboring nodes can be selected to be within the region of a given node if both spatial and temporal criteria are satisfied, such as disclosed herein.

By way of example, the region of interest for each given node may be orthogonally projecting onto a plane tangential to the given node. With this projection a two-dimensional conduction velocity vector is estimated for the given node in the projection of the region of interest based on analysis of the activation computed at the given node relative to other nodes residing in the region of interest. A 3D conduction velocity vector for the given node is then estimated on the original 3D surface, such as by projecting the 2D velocity vector (in the 2D projection) back to the original 3D space, e.g., corresponding to surface mesh.

In the example where surface meshes are used, the estimated local CV vector may be considered an apparent velocity because, for example, the computed speed and direction in the velocity vector for a given node are a combination of activation wave front velocities from the entire local myocardium mass within the region of such given node. The resulting conduction velocity map provides a local vector for each of the nodes that includes speed and/or propagation direction for the nodes in each region of interest over one or more time intervals. The conduction velocity map thus provides an efficient estimate of propagation pattern.

In some examples, the projection from the 2D domain to the 3D domain may be guided by aligning one or more anatomical landmarks (e.g., on the 3D cardiac surface). Additionally, depending on the relative density of the mesh structures in 2D and 3D domains, interpolation may be applied to project and fit computed 2D conduction velocity data for nodes in 2D space (e.g., a given distribution of nodes) to corresponding velocity data at a distribution of nodes across an anatomical 3D mesh (e.g., a different distribution of nodes). Such interpolation may be from a dense distribution (in 2D space) to a more sparse distribution of nodes (in 3D space) or from a sparse distribution (in 2D space) to more dense node distribution (in 3D space). This allows the calculated velocity values to be visualized on detailed anatomy geometry (e.g., 3D cardiac surface geometry), such as may be derived from an imaging modality (e.g., CT and/or MRI).

At 20, one or more pattern maps are generated, to facilitate locating specific tachycardia propagation patterns. As an example, one or more rhythm features can be derived from applying mathematical operators to the conduction velocity computed at 18. For instance, the maps may include direction maps, speed maps, dispersion maps and rotation maps which may be visualized on a display, such as shown in FIGS. 5-13 herein. The type of map and one or more time interval(s) may be selected in response to a user input, for example.

As one example, dispersion features are computed by applying the divergent operator to the conduction velocity vector over one or more time intervals. A corresponding dispersion map (or maps) can be output (as an electrical signal via an output port) to a display device to render a corresponding visualization of the dispersion map(s). The resulting map can visualize divergent and collision areas, such as to help diagnose of focal tachycardias and isthmus barriers.

As another example, rotation features are computed by applying the curl operator to the conduction velocity vector. A corresponding rotation map (or maps) can be output (as an electrical signal via an output port) to a display device to render a corresponding visualization of the rotation map(s). The resulting rotation map can visualize clockwise and counter-clockwise rotations, such as to help diagnose macro-reentrant tachycardia and rotation areas.

At the end of the process, three fields are computed: the CV vector field, the divergence, and the curl fields. The aim of the proposed propagation pattern mapping tool is to compute a CV vector field and derive from it the divergence and curl fields on the 3-D mesh.

Conduction Velocity (CV) Mapping

FIG. 2 is a flow diagram depicting an example method 50 for performing conduction velocity mapping (e.g., corresponding to 16 of FIG. 1). Cardiac CV may be mapped on the entire muscle (or one or more spatial regions of interest) using vector field obtained with spatial coordinates of the nodes on the 3D mesh and the timing data for one or more time intervals. As an example, for each respective node $n_i$, an ROI is defined around the given node. Then, this local surface is orthogonally projected onto the 2D plane tangential to it at $n_i$. The 2D velocity vector $v_i$ is estimated with a local model using either the linear or the quadratic WF shape hypothesis. This vector is then projected onto the original space to get the 3D vector $V_i$ that is tangential to the 3D mesh at the given node. This process is repeated for each node on the entire surface or a portion thereof, which may be of particular interest.

Selection of the Region of Interest (ROI)

At 52, an ROI is selected for a given node $n_i$. As one example of a 2D reference technique, a ROI is selected around the given node $n_i$ regarding spatial and temporal axes. First, the neighboring nodes are identified spatially using the triangulation of the mesh. For example, the first and second-ranks (spatially) neighboring nodes are selected for each respective node $n_i$. For instance, first rank nodes are directly connected to the given node $n_i$ by one edge and second rank nodes are connected to the given node by two contiguous edges.

Next, a temporal selection is performed with respect to the given node $n_i$, such as to ensure the continuity of the propagation in case of reentrant circuits and thereby enable estimation of a realistic CV vector field. For example, spatially selected neighboring nodes for which the activation is too delayed (e.g., delayed an amount greater than a time threshold) from the activation at $n_0$ are discarded. For example, in contrast to using an arbitrary temporal threshold, in this example, temporal selection is done automatically based on the cycle length of the activation $t_{cycle}$. The cycle length may be computed as a time between sequential activations or some other identifiable signal feature between sequential activations. As a further example, neighboring node $n_j$, activated at time $t_j$ is selected to be part of the region of the given node $n_0$ activated at time $t_0$ if:

$$\begin{cases} |t_j - t_0| \le |t_j - t_0 - t_W|, & t_j > t_0 \\ |t_j - t_0| \le |t_j - t_0 + t_W|, & t_j \le t_0 \end{cases} \quad (1)$$

where $t_w$ is the duration of the time window of interest.

For example, the time window $t_w$ is set based on an estimated cycle length of the arrhythmia, such as estimated from a body surface ECG (e.g., a standard 12 lead ECG) or from the unipolar electrograms (e.g., on the body surface or reconstructed onto the cardiac envelope of interest). The time window may be automatically determined or it may be set in response to a user input. At the end of this spatio-temporal ROI selection, the region of interest centered on node $n_0$ is composed of N neighboring nodes. This automated ROI selection method further enables selecting the nodes without an arbitrary threshold that could lead to artifactual results if they are badly identified while preserving the local aspect of the estimation. In some examples, if the resulting number of neighboring nodes in region of interest is less than a predetermined number, the conduction velocity vector may not be computed for the given node. The predetermined number can be fixed number or set in response to a user input, such as to ensure a sufficient number of neighboring nodes in each neighborhood of the given node. In other examples, the size of the neighborhood may be expanded.

Estimation of the Delays

At 54, delays are estimated. In some examples, the delays are more relevant than the activation time marker placement. Accordingly, the delays are included in the example estimation for non-invasive reconstruction of unipolar electrograms (EGMs). The quality of the CV vector estimation depends on the number of neighbors in the region of interest around $n_0$, i.e., N. The adding of the activation time delays between the given node and its neighbors increases the redundancy of the temporal information and so the accuracy of the estimation.

To mitigate uncertainty of the placement of the activation time markers on unipolar EGMs, delays are estimated, for example, using Shors' method, such as disclosed in S. M. Shors, et al., "A method for determining high-resolution activation time delays in unipolar cardiac mapping," *IEEE Trans. Biomed. Eng.*, vol. 43, no. 12, pp. 1192-1196, 1996. By way of example, to calculate the delays, the delay is estimated by applying the Hilbert transformation to the cross-correlation between the unipolar reconstructed EGM of a neighbor node n belonging to the ROI and the given node $n_0$. The time of the maximum correlation correspond to the delay between these two nodes. The corresponding delay $\tau$ is the timing for which this transform is equal to zero. The delay may be estimated independently of determining the orthogonal projection (i.e., the delay may be computed prior to identifying the plane tangential to the ROI).

Orthogonal Projection of the Region of Interest

At 56, an orthogonal projection of the ROI is computed. For example, a non-destructive local projection of the ROI (selected at 52) is used. From the geometry of the 3D mesh obtained with high-density electroanatomic map and the local aspect of the ROI, for example, the curvature may be assumed low or negligible. Thus, to estimate the 3-D CV vector at $n_0$, an orthogonal projection of the N nodes onto the plane $\Pi_0$ tangential at $n_0$ to its region of interest. The use of a local tangential plane is more appropriate than a global tangential plane for less smooth surface geometries, such as atria.

As one example, as the region of interest is a part of an ellipsoid centered on the given node $n_0$, the normal vector of $\Pi_0$ is collinear to one of the three semi-principal axes of the ROI ellipsoid. Hence, an efficient way to estimate the normal vector of the tangential plane is to use singular value decomposition applied on all the 3-D coordinates of the N neighboring nodes for the given node $n_0$ (e.g., wherein N is the remaining neighboring nodes that have not been removed during 52). For example, let $P_0 = [p_{0,x}\ p_{0,y}\ p_{0,z}]$ be the 3×3 orthonormal transfer matrix obtained from this decomposition. Then, locally, it is assumed the curvature is the lowest spatial dispersion of the ROI. As a result, with the conventional ordering for singular value decomposition, the two first vectors of the decomposition span $\Pi_0$, whereas the third vector is orthogonal to $\Pi_0$ which is linked to curvature. Then, the matrix defined by $[p_{0,x}\ p_{0,y}]$ is used to orthogonally project the ROI onto $\Pi_0$. This enables the 2D spatial coordinates of the N nodes in the region of interest and the studied node $n_0$ to be determined as $\{(x,y)\}_{1 \ldots N}$ and $(x_0, y_0)$, respectively.

Estimation of the 3D Local Velocity Vector

At 58, a local 3D velocity vector is estimated for the given node. For example, after determining the orthogonal projection of the ROI (at 54), a 2D local velocity vector for the ROI is estimated (e.g., on the 2D projection plane based spatial and temporal electrical information for each ROI. The spatial and temporal information can include activation times and delays determined for each of the neighboring nodes in the ROI. As an example, the activation times and delays are determined (e.g., at 54) independently prior to or otherwise from the local tangential plane for the ROI on which the 2D local velocity vector is estimated.

In some examples, the spatio-temporal information of the N nodes in the ROI is fit to a polynomial surface model $t=\tilde{t}(x, y)$. This model may be customized with the neighboring activation times and estimated delays, and locally assumes a quadratic activation wave front at $n_0$, such as shown below in Eq. (2).

$$\begin{cases} \tilde{t}(x, y) = a(x-x_0)^2 + b(y-y_0)^2 + \\ \quad c(x-x_0)(y-y_0) + d(x-x_0) + e(y-y_0) + f \\ \tilde{\tau}(x, y) = a(x-x_0)^2 + b(y-y_0)^2 + \\ \quad c(x-x_0)(y-y_0) + d(x-x_0) + e(y-y_0) \end{cases} \quad (2)$$

where $\tilde{\tau}(x,y) = \tilde{t}(x,y) - \tilde{t}(x_0, y_0)$.

In some examples, if N is greater than 3 (N>3), the model parameters (e.g., a, b, c, e, and f) are estimated by minimizing the least square errors between 1) the recorded activation times of the N nodes in the region of interest $\{t\}_{1 \ldots N}$ and the model estimated $\{\tilde{t}(x,y)\}_{1 \ldots N}$; and 2) the estimated delays $\{\tau\}_{1 \ldots N}$ and the model estimated $\{\tilde{\tau}(x,y)\}_{1 \ldots N}$, such as shown in the example of Eq. (3):

$$\min_{a,b,c,\ldots,f} \sum_{1}^{N} [(\tilde{t}(x, y) - t)^2 + (\tilde{\tau}(x, y) - \tau)^2] \quad (3)$$

The local 2D velocity vector $w_0$ for the ROI then may be calculated by applying the 2D spatial gradient $\nabla$ on $\tilde{t}$, estimated at $n_0$, such as demonstrated in Eq. (4):

$$w_0 = \frac{\nabla \tilde{t}(x, y)}{\|\nabla \tilde{t}(x, y)\|^2}\bigg|_{(x=x_0, y=y_0)} = \begin{bmatrix} \frac{d}{d^2+e^2} \\ \frac{e}{d^2+e^2} \end{bmatrix} \quad (4)$$

Finally, the 3-D velocity vector $v_0$ is directly obtained from the projection of $w_0$ back on to the original space with $[p_{0,x}\ p_{0,y}]$ (5).

$$v_0 = [p_{0,x} p_{0,y}] \cdot w_0 \quad (5)$$

At 60, a determination is made whether there are additional nodes across the surface for which the conduction velocity is to be determined. In some examples, the set of nodes may include the entire surface or, in other examples, it may be for nodes distributed across the surface corresponding to one or more regions (e.g., an atrial region, both atria, ventricle or ventricles etc.). If there are more nodes, the method proceeds to 62 in which the next node is identified as the given node $n_0$ for which the conduction velocity is to be computed, and the method repeats. This process (e.g., 52-62) is repeated for each node of interest across the 3-D mesh. At the end of this process, in response to determining that there are no additional nodes, the 3-D CV vector field is defined with a velocity, v, at each node and the value is stored in memory and used to generate a CV map at 64 for each time index in the selected one or time intervals. For example, the each node can include a velocity vector for each time index, including both a direction of propagation value and apparent local speed value associated with each respective node. At 64, the corresponding conduction velocity map may thus be generated and presented on a display based on the stored CV data, such as disclosed herein.

Rhythm Feature Mapping

FIG. 3 is a flow diagram depicting an example of a method 100 to perform rhythm feature mapping (e.g., corresponding to the function 18 of FIG. 1). The method 100 may be implemented as machine readable instructions, which are executable by one or more processors. The method 100 can determine local propagation direction vectors to provide direction and/or speed maps. The method 100 can also be implemented to provide dispersion and/or rotation maps. Such maps thus can visualize on a cardiac surface and thereby identify tachyarrhythmias pattern features, such as rotor or ectopic foci, with greater specificity than traditional activation maps.

At 102, an orthogonal projection of the ROI and the CV vector (from FIG. 2) are computed. For example, the method 100 follows and is based on computation of conduction velocity, such as may be determined according to the method 50 of FIG. 2. Additionally, the orthogonal projection for each ROI may be implemented as described at 56 of CV mapping method 50 of FIG. 2. A purpose of the method 100 is to estimate the divergence and curl functions from the CV vector field to provide additional information associated with wave fronts propagating across the cardiac surface.

At 104, the mathematical divergent (div) of the unitary CV vector is computed. The div of the unitary CV vector ($U_0$) may be computed based on the CV vectors determined for each of nodes in its local 2D projection over one or more time intervals. At 106, the mathematical curl (rot) of the unitary CV vector $U_0$ is computed. The curl of the unitary CV vector $U_0$ may be computed based on the CV vectors determined for each of nodes in its local 2D projection over one or more time intervals.

By way of example let $U_0=\{u\}_{1\ldots N}$ be the unitary CV vector field respectively associated with $\{v\}_{1\ldots N}$, the CV vectors of the N nodes belonging to the region of interest of a given node $n_0$. It is assumed that the local curvature of the region of interest is low. It further may be assumed that the N vectors of $U_0$ are coplanar within the local plane $\Pi_0$. In these conditions, estimating the local curl and divergence in the 3-D Euclidian basis amounts to estimating them in the orthonormal basis, such as may be defined by the triplet $P_0=[p_{0,x}\ p_{0,y}\ p_{0,z}]$ as demonstrated in Eqs. (6) and (7) below with $W_0=\{w\}_{1\ldots N}$, the unitary CV vectors $U_0$ expressed in the basis defined by $P_0$, as follows:

$$\mathrm{div}(U_0)=\mathrm{div}(W_0) \tag{6}$$

$$\mathrm{rot}(U_0)=P_0\cdot\mathrm{rot}(W_0) \tag{7}$$

In some examples, assuming the 3D mesh is spherical, the curl operator is modified to get the vector $(b_{i_x}\wedge b_{i_y})$ outward, where the vector $(b_{i_x}\wedge b_{i_y})$ is the third vector component of the left-singular matrix obtained via singular value decomposition. Hence, as in 2D, an outward curl vector for a given node represents to a counter-clockwise rotation whereas an inward vector represents to a local clockwise rotation for such node.

At 108, local operators for the div and curl expressions are estimated. To estimate locally the divergent $\mathrm{div}(W_0)$ and the curl $\mathrm{rot}(W_0)$, a linear model linking each direction component of the local direction of the ROI is parameterized. For example, the linear model can be used to link the spatial coordinates of the N nodes in $P_0$, $\{(x, y, z)\}_{1\ldots N}$, to $W_0$. As these unitary vectors are assumed to be coplanar and belong to the plane $\Pi_0$ defined by the normal vector $p_{0,z}$, the variations along this normal axis are equal to zero. Thus, to estimate $\mathrm{div}(W_0)$ and $\mathrm{rot}(W_0)$, two 2D linear propagation models can be used, namely $\tilde{w}_x$ and $\tilde{w}_y$, linking respectively the component of $W_0$ along $p_{0,x}$ (8) and $p_{0,y}$ (9) with the 2D spatial coordinates x and y such as follows:

$$\tilde{w}_x(x,y)=\alpha_x(x-x_0)+\beta_x(y-y_0)+\gamma_x \tag{8}$$

$$\tilde{w}_y(x,y)=\alpha_y(x-x_0)+\beta_y(y-y_0)+\gamma_y \tag{8}$$

where $\alpha_x$, $\alpha_y$, $\beta_x$, $\beta_y$, $\gamma_x$ and $\gamma_y$ are the model coefficients.

Then, the model components are calculated by minimizing the least square error between respectively the model estimated unitary vector components $\tilde{w}_x$ and $\tilde{w}_x$ as in Eq. (10) for the first model, and between $\tilde{w}_y$ and $w_y$ as in Eq. (11) for the second model.

$$\min_{\alpha_x,\beta_x,\gamma_x}\sum_1^N[(\tilde{w}_x(x,y)-w_x)^2] \tag{10}$$

$$\min_{\alpha_y,\beta_y,\gamma_y}\sum_1^N[(\tilde{w}_y(x,y)-w_y)^2] \tag{11}$$

From this model, each of the partial derivatives in (6) and (7) are estimated at $n_0$ to get respectively its local divergence (12) and curl (13) in the original space at the given node $n_0$, such as may be expressed as:

$$\mathrm{div}(U_0)=\alpha_x+\beta_y \tag{12}$$

$$\mathrm{rot}(U_0)=(\alpha_y-\beta_x)p_{0,z} \tag{13}$$

The systems and methods disclosed herein facilitate non-invasively identification of atrial tachycardia mechanisms. This can be performed as a bedside application to establish the strategy before the procedure. This is accomplished by one or more of the following:

a. combining of signal averaging and a generic (or patient-specific) atrium mesh for non-invasive propagation mapping;

b. conduction velocity mapping (direction and speed maps)

c. rhythm features mapping (dispersion and rotation maps); and/or d. combining two or more of these maps to facilitate the mechanism identification.

Figure 4:
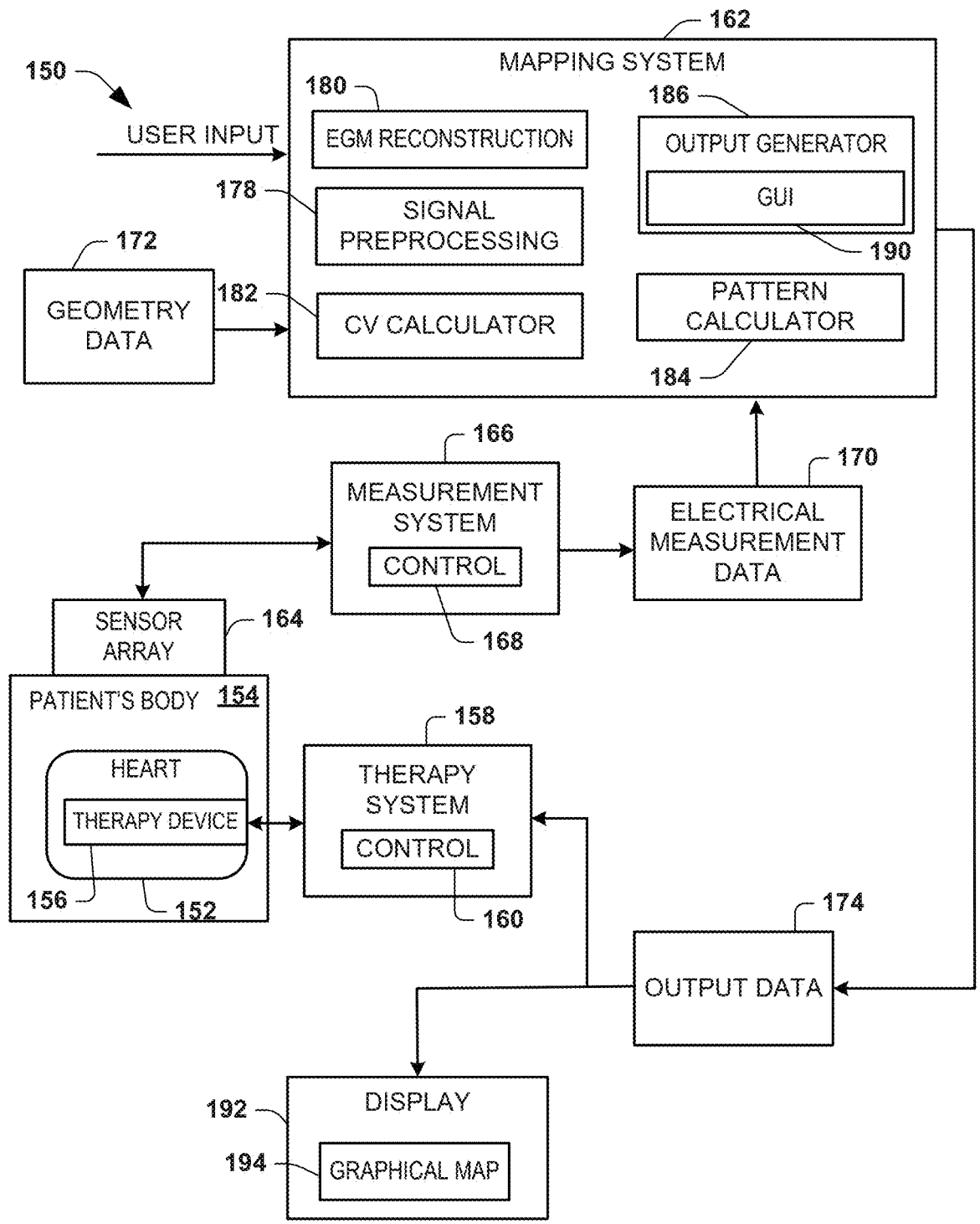
FIG. 4 depicts an example of a system for diagnosis and/or treatment.

FIG. 4 depicts an example of a system 150 that can be utilized for performing diagnostics and/or treatment of a patient. In some examples, the system 150 can be utilized to generate one or more corresponding electrophysiological maps 194 on a display 192, such as to visualize spatial and temporal electrical activity for a patient's heart 152. The system may be used in real time as part of a diagnostic procedure (e.g., an electrophysiology study) to help assess the electrical activity and identify arrhythmia drivers for the patient's heart. Additionally or alternatively, the system 150 can be utilized as part of a treatment procedure, such as to help a physician determine parameters for delivering a therapy to the patient (e.g., delivery location, amount and type of therapy) based on one or more identified arrhythmia drivers.

As an example, a catheter, such as a pacing or an ablation catheter, having one or more therapy delivery devices 156 affixed thereto can be inserted into a patient's body 154 (e.g., into or onto) the patient's heart 152, endocardially or epicardially. Various types and configurations of therapy delivery devices 156 that can be utilized, which can vary depending on the type of treatment and the procedure. For instance, the therapy device 156 can be configured to deliver electrical therapy, chemical therapy, sound wave therapy, thermal therapy or any combination thereof. The placement of the device 156 can be guided based on mapping conduction velocity and/or rhythm patterns across the cardiac surface as disclosed herein. The guidance can be automated, semi-automated or be manually implemented based on information provided.

As a further example, the delivery device 156 can include one or more electrodes located at a tip of an ablation catheter configured to generate heat for ablating tissue in response to electrical signals (e.g., radiofrequency energy) supplied by a therapy system 158. In other examples, the therapy delivery device 156 can be configured to deliver cooling to perform ablation (e.g., cryogenic ablation), to deliver chemicals (e.g., drugs), ultrasound ablation, high-frequency ablation, or a combination of these or other therapy mechanisms. In still other examples, the therapy delivery device 156 can include one or more electrodes located at a tip of a pacing catheter to deliver electrical stimulation, such as for pacing the heart, in response to electrical signals (e.g., pacing pulses) supplied by a therapy system 158. Other types of therapy can also be delivered via the therapy system 158 and the invasive therapy delivery device 156 that is positioned within the body.

In some examples, the therapy system 158 can be located external to the patient's body 154 and be configured to control therapy that is being delivered by the device 156. For instance, the therapy system 158 includes controls (e.g., hardware and/or software) 160 that can communicate (e.g., supply) electrical signals via a conductive link electrically connected between the delivery device (e.g., one or more electrodes) 156 and the therapy system 158. The control system 160 can control parameters of the signals supplied to the device 156 (e.g., current, voltage, repetition rate, trigger delay, sensing trigger amplitude) for delivering therapy (e.g., ablation or stimulation) via the electrode(s) 154 to one or more location of the heart 152. The controls 160 can set the therapy parameters and apply stimulation based on automatic, manual (e.g., user input) or a combination of automatic and manual (e.g., semiautomatic) controls. One or more sensors (not shown) can also communicate sensor information (e.g., electrical and/or thermal measurements) back to the therapy system 158. The position of the device 156 relative to the heart 152 can be determined and tracked intraoperatively via an imaging modality (e.g., fluoroscopy, x-ray), a mapping system 162, direct vision or the like. The location of the device 156 and other therapy parameters thus can be combined and used by the controls 160 to determine corresponding therapy parameter data.

Before, during and/or after delivering a therapy via the therapy system 158, another system or subsystem can be utilized to acquire electrophysiology information for the patient. In the example of FIG. 4, a sensor array 164 includes one or more electrodes that can be utilized for recording patient electrical activity. As one example, the sensor array 164 can correspond to a high-density arrangement of body surface sensors (e.g., greater than approximately 200 electrodes) that are distributed over a portion of the patient's torso for measuring electrical activity associated with the patient's heart (e.g., as part of an electrocardiographic mapping procedure). Examples of a high-density body surface non-invasive apparatus that can be used as the sensor array 716 are shown and described in U.S. Pat. No. 9,655,561 and international publication No. WO 2010/054352, which are incorporated herein by reference. Other arrangements and numbers of sensing electrodes can be used as the sensor array 164. As an example, the array can be a reduced set of electrodes, which does not cover the patient's entire torso and is designed for measuring electrical activity for a particular purpose (e.g., an array of electrodes specially designed for analyzing AF and/or VF) and/or for monitoring a predetermined spatial region of the heart.

One or more sensors may also be located on the device 156 that is inserted into the patient's body. Such sensors can be utilized separately or in conjunction with the non-invasive sensors 164 for mapping electrical activity for an endocardial surface, such as the wall of a heart chamber, as well as for an epicardial surface. Additionally, such electrode can also be utilized to help localize the device 156 within the heart 152, which can be registered into an image or map that is generated by the system 150. Alternatively, such localization can be implemented in the absence of emitting a signal from an electrode within or on the heart 152.

In each of such example approaches for acquiring patient electrical information, including invasively, non-invasively, or a combination of invasive and non-invasive sensing, the sensor array(s) 164 provide the sensed electrical information (e.g., time-varying, unipolar electrical potential measurements distributed across the thorax) to a corresponding measurement system 166. The measurement system 166 can include appropriate controls and signal processing circuitry 168 for providing corresponding measurement data 170 that describes electrical activity detected by the sensors in the sensor array 164. The measurement data 170 can include analog and/or digital information.

The control 168 can also be configured to control the data acquisition process (e.g., sample rate, line filtering) for measuring electrical activity and providing the measurement data 170. In some examples, the control 168 can control acquisition of measurement data 170 separately from the therapy system 158 operation, such as in response to a user input. In other examples, the measurement data 170 can be acquired concurrently with and in synchronization with delivering therapy by the therapy system, such as to detect electrical activity of the heart 152 that occurs in response to applying a given therapy (e.g., according to therapy parameters). For instance, appropriate time stamps can be utilized for indexing the temporal relationship between the respective measurement data 170 and therapy parameters use to deliver therapy as to facilitate the evaluation and analysis thereof.

Since the measurement system 166 can measure electrical activity of a predetermined region or the entire heart concurrently (e.g., where the sensor array 164 covers the entire thorax of the patient's body 154), the resulting output data (e.g., visualizing attributes of identified conduction velocity and associated rhythm patterns, such as propagation, rotational activity and/or other characteristsics) thus can also represent concurrent data for the predetermined region or the entire heart in a temporally and spatially consistent manner. The one or more time interval for which the output data/maps are computed can be selected based on user input (e.g., selecting a timer interval from one or more waveforms). Additionally or alternatively, the selected intervals can be synchronized with the application of therapy by the therapy system 158.

The mapping system 162 includes signal processing methods 178 to preprocess the electrical measurement data 170. For example, such preprocessing implement any of the types of preprocessing disclosed at 12 in FIG. 1. For instance the pre-processing computes an average beat on each input channel (lead) from the sensor array 164.

For the example where the electrical measurement data is obtained non-invasively (e.g., via body surface sensor array 164), electrogram reconstruction 180 can be programmed to compute an inverse solution and provide corresponding reconstructed electrograms (e.g., unipolar electrograms) on a cardiac envelope based on the preprocessed electrical signals (from signal preprocessing 178) and the geometry data 172. For example, the reconstructed electrograms thus can be estimated for each of the nodes on across a 3D mesh surface that defines a cardiac envelope over one or more time intervals.

Examples of inverse algorithms that can be implemented by the electrogram reconstruction 180 in the system 150 include those disclosed in U.S. Pat. Nos. 7,983,743 and 6,772,004, which are incorporated herein by reference. The EGM reconstruction 180 thus can reconstruct the body surface electrical activity measured via the sensor array 164 onto a multitude of locations (nodes) on the cardiac envelope (e.g., greater than 1000 locations, such as about 2000 locations or more). In some examples, the EGM reconstruction 180 of the mapping system 162 can compute electrical activity over a sub-region of the heart based on electrical activity measured invasively, such as via a basket catheter or other form of measurement probe.

As disclosed herein, the cardiac envelope can correspond to a three dimensional surface geometry corresponding to a patient's heart, which surface can be epicardial or endocardial. Alternatively or additionally, the cardiac envelope can correspond to a three-dimensional geometric surface that resides between the epicardial surface of a patient's heart and the surface of the patient's body where the sensor array 164 has been positioned. Additionally, the geometry data 172 that is utilized by the electrogram reconstruction 180 can correspond to actual patient anatomical geometry, a preprogrammed generic model or a combination thereof (e.g., a model that is modified based on patient anatomy).

As an example, the geometry data 172 may includes data representing the cardiac envelope as a three dimensional polygonal mesh, including nodes connected by edges, as well as coordinates for the locations on the patient's torso where each of the sensing electrodes in the array 164 reside, such as derived from image data acquired for the patient. For instance, image processing can include extraction and segmentation of anatomical features, including one or more organs and other structures, from a digital image set. Additionally, a location for each of the electrodes in the sensor array 164 can be included in the patient geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array, such as a digitizer or manual measurements.

As mentioned above, the geometry data 172 can correspond to a mathematical model, such as can be a generic model or a model that has been constructed based on image data for the patient. Appropriate anatomical or other landmarks, including locations for the electrodes in the sensor array 164 can be identified in the geometry data 172 to facilitate registration of the electrical measurement data 170 and performing the electrogram reconstruction 180 thereon. The identification of such landmarks can be done manually (e.g., by a person via image editing software) or automatically (e.g., via image processing techniques).

By way of further example, the geometry data 172 can be acquired using nearly any imaging modality based on which a corresponding representation of the 3D geometrical surface can be constructed (e.g., a generic or patient-specific mesh structure), such as a triangular mesh of mesh of other size polygons as described herein. Such imaging may be performed concurrently with recording the electrical activity that is utilized to generate the patient measurement data 170 or the imaging can be performed separately (e.g., before or after the measurement data has been acquired).

The mapping system 162 includes a CV calculator 182 programmed (e.g., executable software instructions corresponding to method 50) to compute a three-dimensional conduction velocity map for nodes across the cardiac envelope. By way of brief example, the CV calculator includes an ROI calculator to determine a region of interest around a given node of the plurality of nodes on the surface of interest. The CV calculator further includes a 3D-to-2D projection component programmed to project the region of interest around the given node from the surface of interest onto 2D surface (e.g., a plane) tangential to the given node. The CV calculator further includes a 2D CV calculator to estimate a two-dimensional CV vector for the given node based on analysis of the electrophysiological signal for the given node relative to other nodes in the ROI. The CV calculator 182 further is programmed to estimate the 3D CV vector for the given node on the 3D surface of interest (e.g., of the heart surface) based on the 2D CV vector.

As a further example, the CV calculator can compute the CV at each of nodes distributed across the mesh surface that represents the cardiac envelope, as provided by the geometry data 172. The CV calculator 182 may operate to compute the CV map data in real-time (e.g., concurrently) with acquisition of body surface electrical potential measurements (e.g., by sensor array 164). Alternatively or additionally, the CV calculator 182 may operate off-line to compute the CV map data following the acquisition of body surface electrical potential measurements and reconstruction of the electrograms by EGM reconstruction 180.

The mapping system 162 also may include a pattern calculator 184 programmed (e.g., executable software instructions corresponding to method 100) to compute one or more pattern feature maps based on the conduction velocity (e.g., computed by CV calculator 182). For example, the pattern calculator 184 may compute one or more pattern feature maps, such as including propagation direction, speed, rotation and/or dispersion, such as disclosed herein.

The mapping system 162 includes an output generator 186 that is programmed to generate output data 174 corresponding to graphical maps (e.g., computed electrophysiological information spatially represented on a cardiac envelope) based on computed output data, such as disclosed herein above. For example, the output generator 186 can convert the computed map data (e.g., CV and/or pattern map data) into output data (e.g., primitives) to drive a graphics pipeline of a computing system on which the mapping system 162 is implemented. The output data 174 can include data provided to the display 192 for visualization of one or more graphical maps 194, such as disclosed herein.

In some examples, the output generator 186 includes a graphical user interface (GUI) 190 to control the output generator and to set one or more parameters associated with the displayed graphical representation, corresponding to an output visualization of the computed map. For example, a user can configure and select various parameters in response to a user input via the GUI 190, such as including selecting a time interval, selecting a type of map (or maps) that is to be presented in the visualization and the like. Additionally, a user can employ the GUI 190 to selectively program one or more parameters (e.g., temporal and spatial thresholds, filter parameters and the like) utilized by the CV calculator 182 and/or pattern calculator 184 and/or to select one or more sample time intervals to set a time duration for the electrical data 170 that is utilized by the mapping system 162.

The output generator 186 thus provides output data 174, which can be used to visualize a corresponding graphical output in a display 192, such as including an electrocardiographic map 194. For example, the system 162 can generate maps and other output visualizations, such as including but not limited to the maps and other output visualizations disclosed herein. The mapping system 162 and its respective functions 178, 180, 182, 184, 186 and 190 can be implemented as machine-readable software code instructions stored in memory and executable by one or more processors of a computer system. The geometry data 172 and measurement data 170 also may be stored in the memory and be accessed by the processor(s) for performing such functions.

Additionally, in some examples, the mapping system 162 can provide the output data 174 to be utilized by the therapy system 158. The control 160 that is implemented can be fully automated control, semi-automated control (partially automated and responsive to a user input) or manual control based on the output data 174. In some examples, the control 160 of the therapy system can utilize the output data 174 to control one or more therapy parameters. As an example, the control 160 can control delivery of ablation therapy to a site of the heart (e.g., epicardial or endocardial wall) based on activation timing or activation wave fronts determined by one or both of the calculators 182 and 184. In other examples, an individual can view the map 194 generated in the display to manually control the therapy system. Other types of therapy and devices can also be controlled based on the output data 174 and corresponding graphical map 194.

FIGS. 5-13 depict examples of GUI 200 that include various output graphical maps that can be generated (e.g., by mapping system 162) to visual electrophysiological information across the surface of a cardiac envelope (e.g., the heart) for different user settings. The GUI 200 includes a GUI control panel with interactive buttons for performing various functions and setting display parameters, such as disclosed herein. In the examples of FIGS. 5-13 the buttons include buttons 210 and 212 for selecting one or more types of tachycardia to visualize on the map, macroreentry and focal, respectively. Buttons 214, 216 and 218 provide for selectively displaying maps relating to cardiac activation, including an activation time map (via button 214), a propagation pattern map (via button 216) and a speed map (via button 218). The speed and direction of propagation can be generated based on conduction velocity calculation methods disclosed herein. As mentioned, the computed maps may be displayed on simplified (e.g., smoothed) geometry or on more detailed anatomy geometry (e.g., true geometry derived from imaging data).

The GUI 200 also includes buttons for selectively displaying rhythm pattern features, including rotation patterns and/or dispersion patterns, across the cardiac surface. For example, a user can selectively activate/deactivate a rotation map (via button 220), as well as counter-clockwise flutter in the rotation map (via button 222) and clockwise flutter in the rotation map (via button 224). The rotation map can be computed, for example, from applying a curl operator to the CV map as disclosed herein. In further examples a user can selectively activate/deactivate a divergent map (via button 226), counter-clockwise flutter in the rotation map (via button 228) and clockwise flutter in the rotation map (via button 230). The divergent map can be computed, for example, to determine the dispersion features by applying divergent operators to the CV map as disclosed herein. One or more intervals of reconstructed electrical data can also be selected by a user in response to a user input activating a select interval button 234 to implement functions for selecting the interval(s) of interest.

Figure 5:
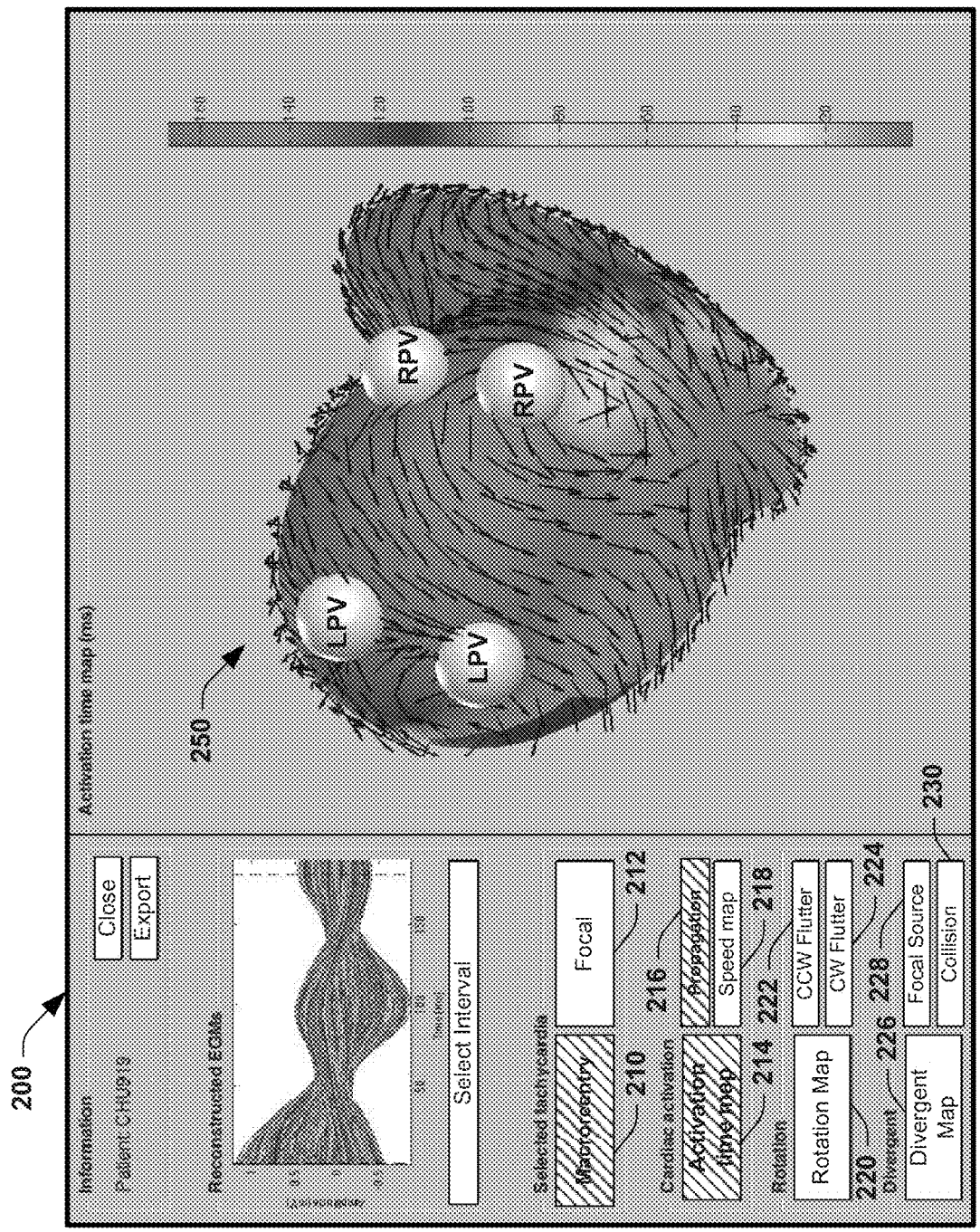
FIG. 5 is a graphical user interface demonstrating an example activation time map showing direction of activation.

FIG. 5 is a graphical user interface demonstrating an example activation time map 250 showing direction of activation. In this example, the macroreentry button 210, activation time map button 214 and propagation button 216 are activated.

Figure 6:
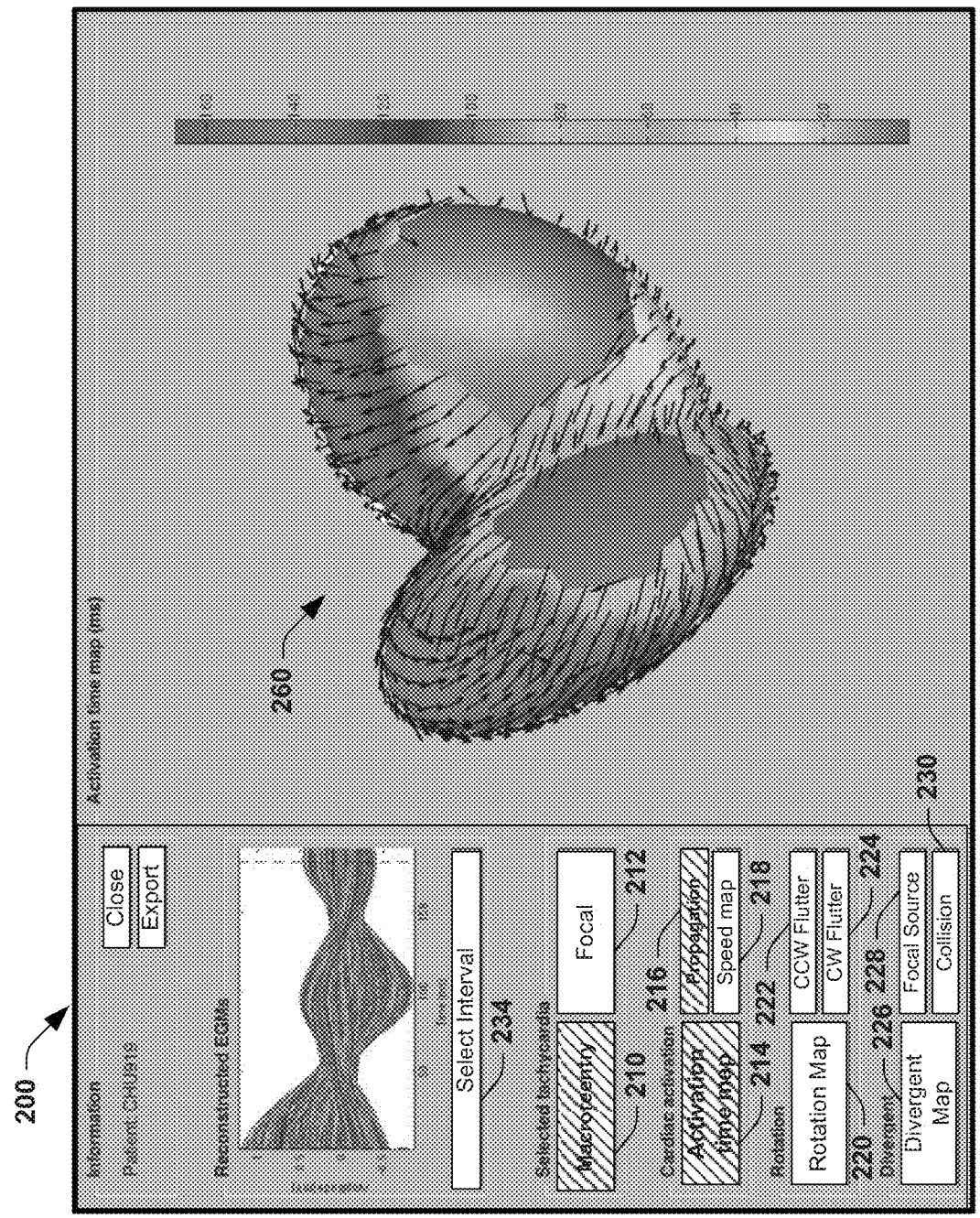
FIG. 6 is a graphical user interface demonstrating an example activation time map showing propagation pattern direction.

FIG. 6 is a graphical user interface demonstrating an example activation time map 260 showing propagation pattern direction. In this example, the macroreentry button 210, activation time map button 214 and propagation button 216 are activated.

Figure 7:
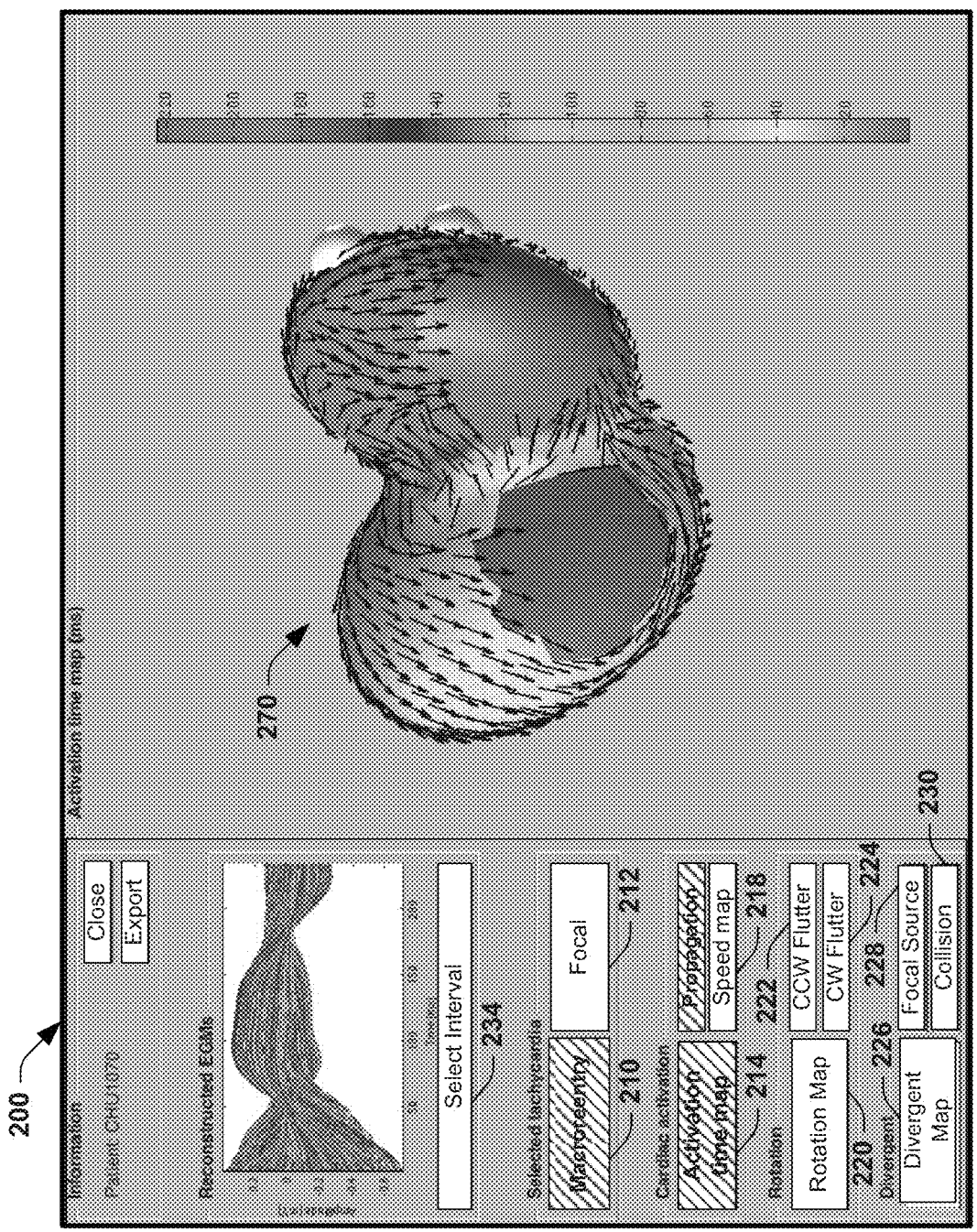
FIG. 7 is a graphical user interface demonstrating an example activation time map showing propagation pattern direction.

FIG. 7 is a graphical user interface demonstrating another example activation time map 270 showing propagation pattern direction. In this example, the macroreentry button 210, activation time map button 214 and propagation button 216 are activated.

Figure 8:
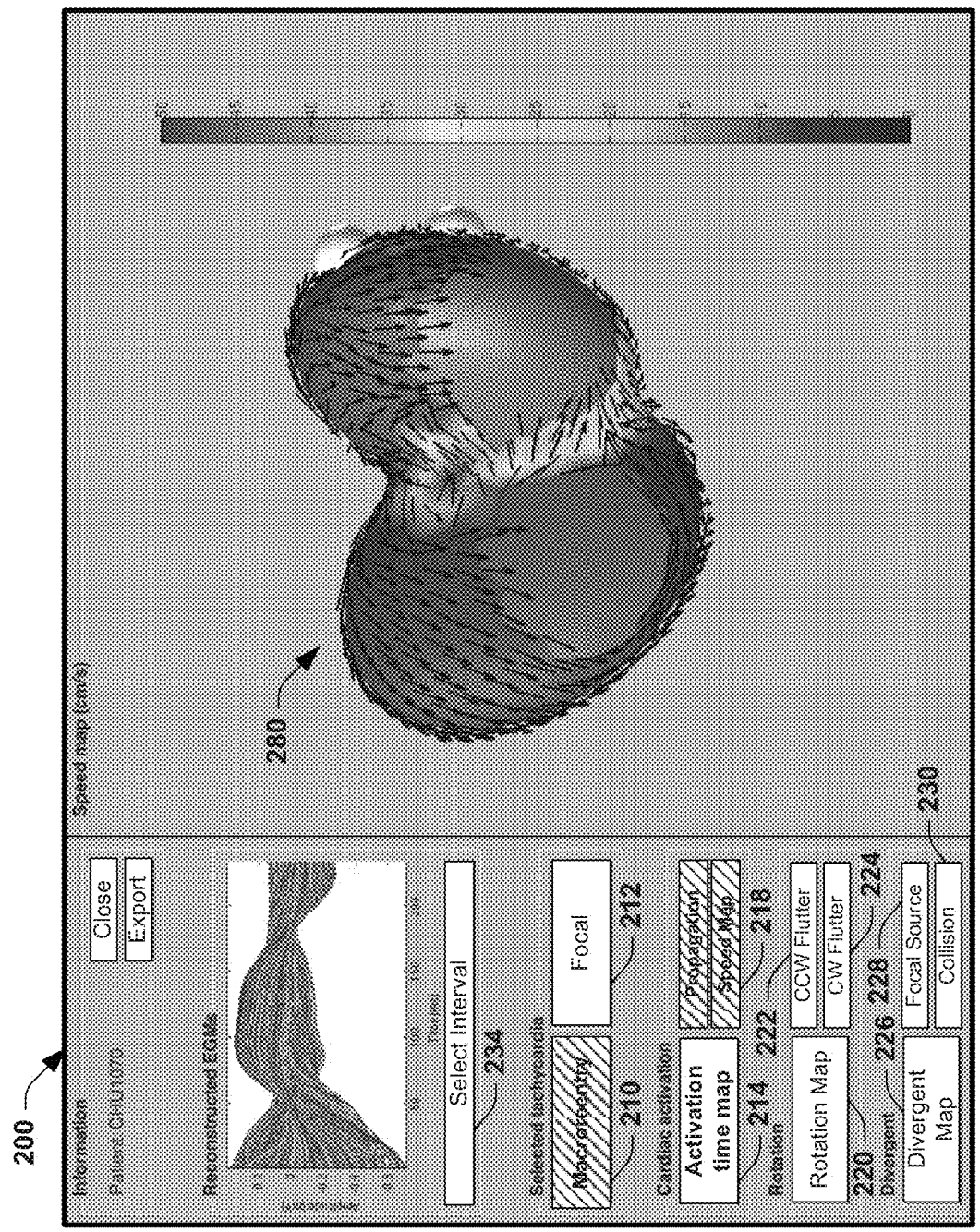
FIG. 8 is a graphical user interface demonstrating an example speed map showing propagation pattern direction and speed.

FIG. 8 is a graphical user interface demonstrating an example of a speed map 280 showing propagation pattern direction and speed across the heart surface. In this example, the macroreentry button 210, propagation button 216 and speed map button 218 are activated.

Figure 9:
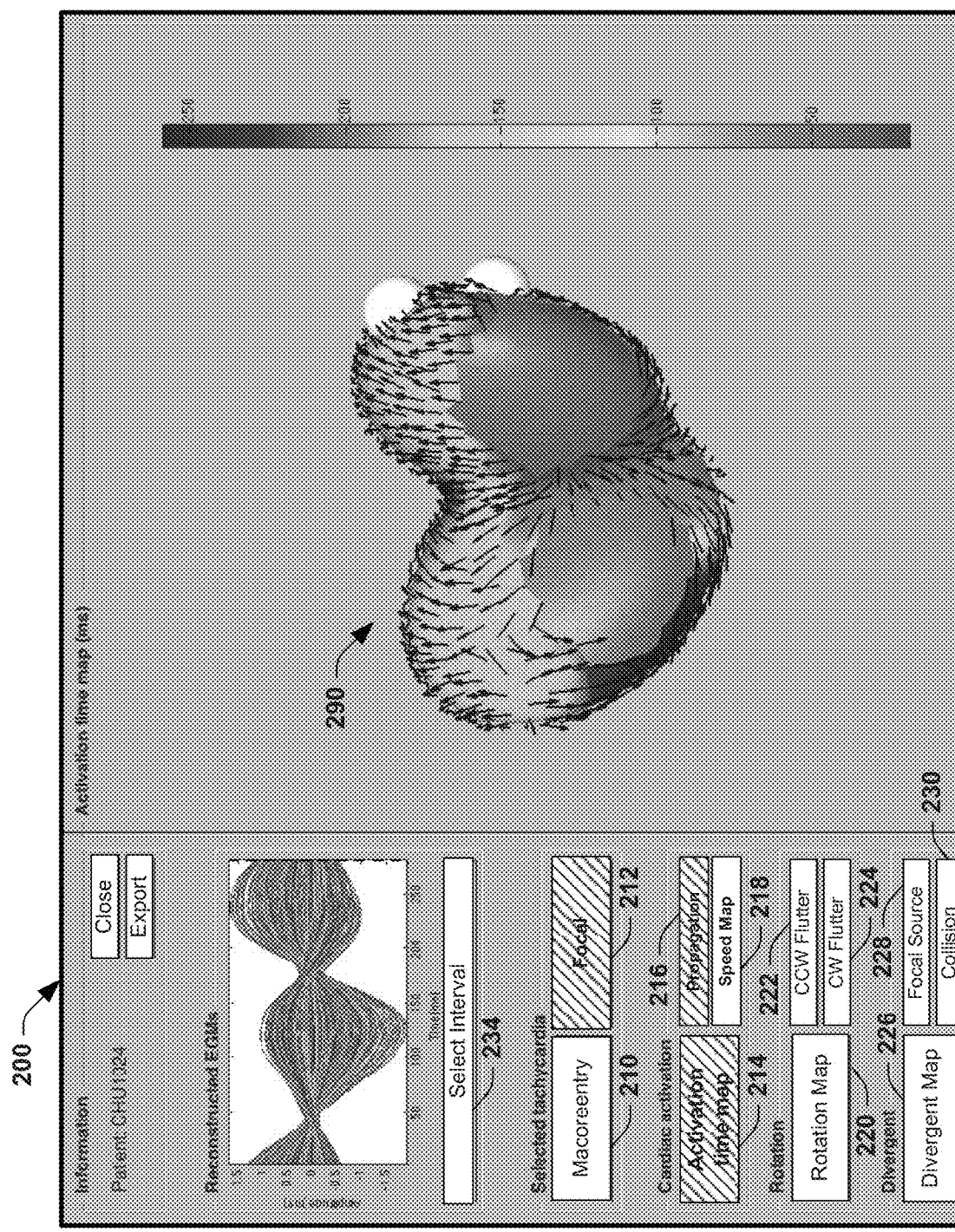
FIG. 9 is a graphical user interface demonstrating an example activation time map showing focal tachycardia and propagation pattern direction.

FIG. 9 is a graphical user interface demonstrating an example of a direction map 290 showing focal tachycardia propagation pattern direction across the heart surface from an anterior-posterior viewing angle. In this example, the focal button 210, activation map button 214 and propagation button 216 are activated.

Figure 10:
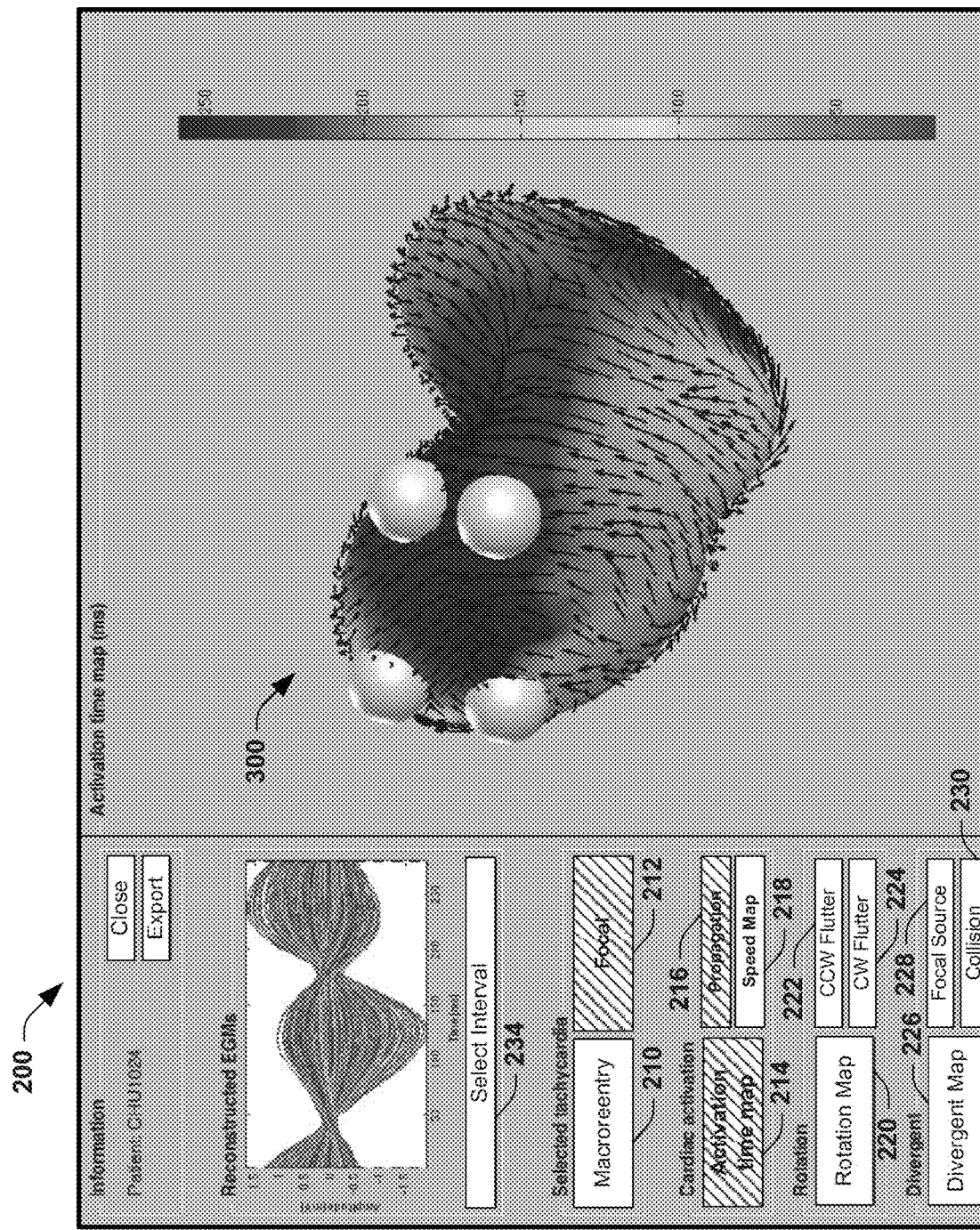
FIG. 10 is a graphical user interface demonstrating an example activation time map showing propagation pattern direction.

FIG. 10 is a graphical user interface demonstrating an example of a direction map 300 showing focal tachycardia propagation pattern direction distributed across the heart surface from a posterior-anterior viewing angle. In this example, the focal button 212, activation map button 214 and propagation button 216 are activated.

Figure 11:
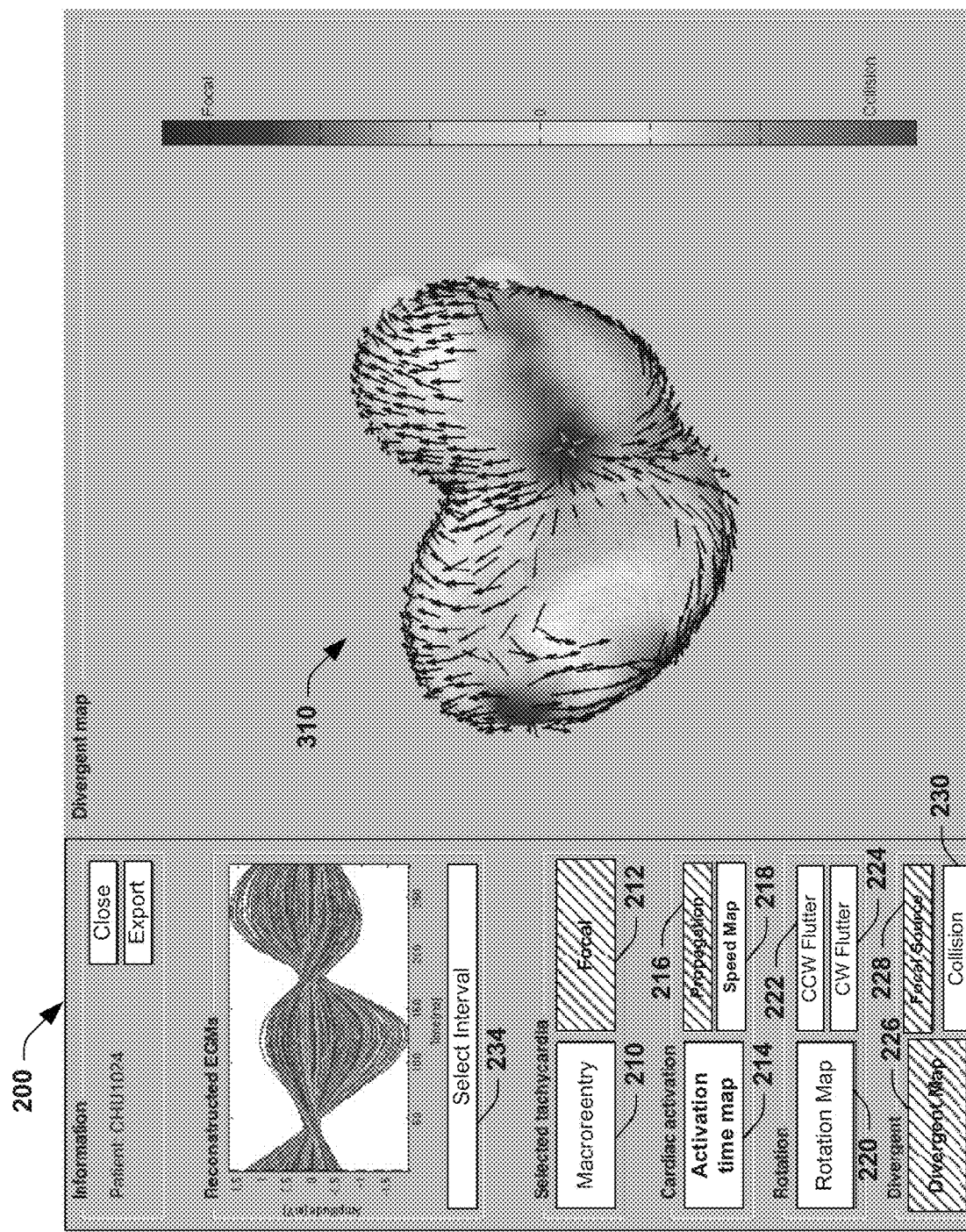
FIG. 11 is a graphical user interface demonstrating an example dispersion map showing propagation pattern direction.

FIG. 11 is a graphical user interface demonstrating an example of a dispersion map 310 showing focal tachycardia propagation pattern direction and focal sources across the heart surface from an anterior-posterior viewing angle. In this example, the focal button 212, propagation button 216, divergent map 226 and focal source button 228 are activated.

Figure 12:
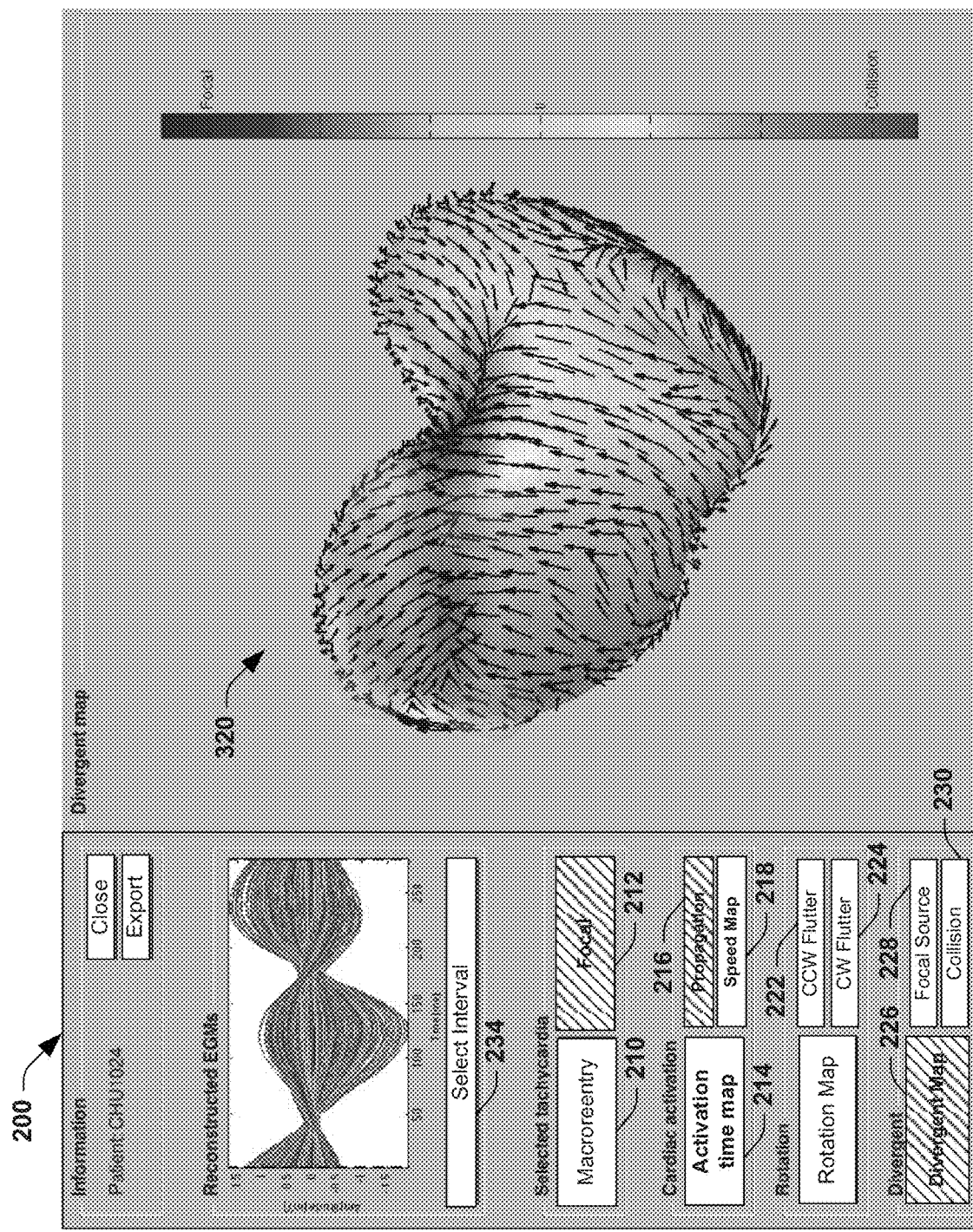
FIG. 12 is a graphical user interface demonstrating an example dispersion map showing propagation pattern direction.

FIG. 12 is a graphical user interface demonstrating an example of a dispersion map 320 showing focal tachycardia propagation pattern direction and wave front dispersion across the heart surface from a posterior-anterior viewing angle. In this example, the focal button 212, and propagation button 216, and divergent map button 226 are activated.

Figure 13:
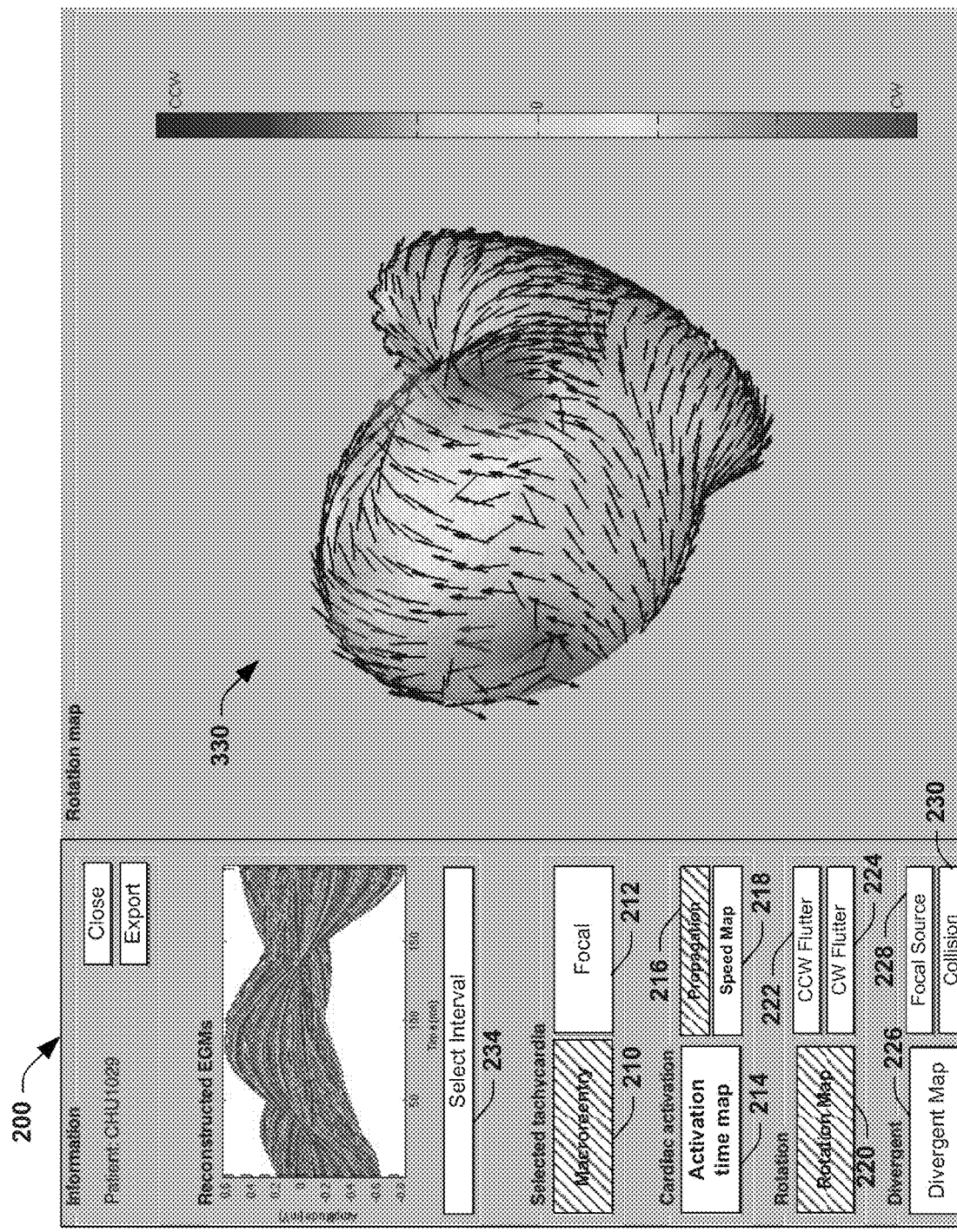
FIG. 13 is a graphical user interface demonstrating an example rotation map showing propagation pattern direction.

FIG. 13 is a graphical user interface demonstrating an example of a rotation map 330 showing rotational tachycardia propagation pattern direction and rotation across the heart surface. In this example, the macroreentry button 210, propagation button 216, and rotation map button 214 are activated.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware.

Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. A method, comprising:
defining a region of interest around a given node on a three-dimensional surface of interest, the defining the region of interest comprising selecting a set of neighboring nodes in the region of interest for the given node according to temporal and spatial criteria with respect to the given node, electrophysiological signals being stored, in memory, for each of a plurality of nodes distributed across the surface of interest;
orthogonally projecting the region of interest for the given node from the surface of interest onto a two-dimensional surface tangential to the given node;
estimating a two-dimensional electrical conduction velocity vector for the given node based on analysis of the electrophysiological signal for the given node relative to other nodes in the region of interest; and
estimating a three-dimensional conduction velocity vector for the given node based on the two-dimensional electrical conduction velocity vector.

2. The method of claim 1, wherein each of the defining, projecting and estimating is repeated for each of the plurality of nodes on the surface of interest to generate a conduction velocity map for each of the plurality of nodes.

3. The method of claim 1, wherein selecting the set of neighboring nodes includes determining a delay between an activation time of the given node and the activation time each of the neighboring nodes in the region of interest,
the delay being compared to a threshold to remove a spatially identified neighboring node from the set of neighboring nodes.

4. The method of claim 3, wherein the threshold is determined for each of the neighboring nodes in the region of interest based on the activation time of the given node, the activation time of the respective neighboring node and a cycle length.

5. The method of claim 1, further comprising generating a feature pattern map based on the estimated three-dimensional conduction velocity vector.

6. The method of claim 5, wherein the feature pattern map comprises at least one of a propagation direction map, a speed map, a rotation map and a dispersion map.

7. The method of claim 5, further comprising determining a unitary conduction velocity vector field for the given node based on the three-dimensional conduction velocity vector.

8. The method of claim 7, wherein generating the feature pattern map further comprises applying a divergence operation to the unitary conduction velocity vector field to determine the feature pattern map as including local dispersion for the given node.

9. The method of claim 7, wherein generating the feature pattern map further comprises applying a curl operation to the unitary conduction velocity vector field to determine the feature pattern map as including rotation for the given node.

10. The method of claim 5, further comprising sending an output signal to drive a display that includes a visualization of the feature pattern map on the three-dimensional surface of interest.

11. The method of claim 5, further comprising controlling delivery of treatment to a heart based on the feature pattern map.

12. The method of claim 1, wherein the electrophysiological signals for each of the plurality of nodes comprise reconstructed electrophysiological signals determined from non-invasively measured electrical signals and geometry data.

13. One or more non-transitory media comprising instructions, which when executed by a processor, perform the method of claim 1.

14. A system comprising:
memory to store machine readable instructions and data, the data comprising electrical data representing electrophysiological signals for a plurality of nodes distributed across a three-dimensional surface of interest; and
one or more processors to access the memory and execute the instructions, the instructions programmed to at least:
determine a region of interest around a given node of the plurality of nodes on the surface of interest, the region of interest being determined to define a set of neighboring nodes in the region of interest for the given node according to temporal and spatial criteria with respect to the given node;
project the region of interest around the given node from the surface of interest onto a two-dimensional surface tangential to the given node;
estimate a two-dimensional electrical conduction velocity vector for the given node based on analysis of the electrophysiological signal for the given node relative to other nodes in the region of interest; and estimate a three-dimensional conduction velocity vector for the given node on the three-dimensional surface of interest based on the two-dimensional electrical conduction velocity vector.

15. The system of claim 14, wherein the instructions are further programmed to repeat the estimate of the three-dimensional conduction velocity vector for each of the plurality of nodes on the surface of interest and to generate a conduction velocity map for each of the plurality of nodes.

16. The system of claim 14, wherein the instructions to determine the region of interest are further programmed to:

determine a delay between an activation time of the given node the activation time each of the neighboring nodes in the region of interest, wherein the delays are computed independent for the neighboring nodes on the three-dimensional surface of interest; and remove a spatially identified neighboring node from the set of neighboring nodes based on the delay relative to a threshold, wherein the threshold is determined for each of the neighboring nodes in the region of interest based on the activation time of the given node, the activation time of the respective neighboring node and a cycle length.

17. The system of claim 14, wherein the instructions are further programmed to generate a feature pattern map based on the estimated three-dimensional conduction velocity vector.

18. The system of claim 17, wherein the feature pattern map comprises at least one of a propagation direction map, a speed map, a rotation map and a dispersion map.

19. The system of claim 17, wherein the instructions are further programmed to determine a unitary conduction velocity vector field for the given node from the three-dimensional conduction velocity vector.

20. The system of claim 19, wherein the instructions to generate the feature pattern map are further programmed to apply a divergence operation to the unitary conduction velocity vector field to determine the feature pattern map as including local dispersion for the given node.

21. The system of claim 19, wherein the instructions to generate the feature pattern map are further programmed to apply a curl operation to the unitary conduction velocity vector field to determine the feature pattern map as including rotation for the given node.

22. The system of claim 17, further comprising a display device to display a graphical map based on at least one of the three-dimensional conduction velocity vector or the feature pattern map on the three-dimensional surface of interest.

23. The system of claim 17, further comprising a therapy system to control delivery of treatment to a heart at least one of the three-dimensional conduction velocity vector or the feature pattern map on the three-dimensional surface of interest.

24. The system of claim 14, further comprising a sensor array to non-invasively measure electrical signals from a body surface to provide electrical measurement data, wherein the instructions are further programmed to reconstruct the electrophysiological signals on to each of the plurality of nodes of the surface of interest based on the electrical measurement data and geometry data.

25. A method, comprising:

defining a region of interest around a given node on a three-dimensional surface of interest, electrophysiological signals being stored, in memory, for each of a plurality of nodes distributed across the surface of interest;

orthogonally projecting the region of interest for the given node from the surface of interest onto a two-dimensional surface tangential to the given node;

estimating a two-dimensional electrical conduction velocity vector for the given node based on analysis of the electrophysiological signal for the given node relative to other nodes in the region of interest;

estimating a three-dimensional conduction velocity vector for the given node based on the two-dimensional electrical conduction velocity vector; and determining a unitary conduction velocity vector field for the given node based on the three-dimensional conduction velocity vector.

26. A system comprising:

memory to store machine readable instructions and data, the data comprising electrical data representing electrophysiological signals for a plurality of nodes distributed across a three-dimensional surface of interest; and one or more processors to access the memory and execute the instructions, the instructions programmed to at least:

determine a region of interest around a given node of the plurality of nodes on the surface of interest;

project the region of interest around the given node from the surface of interest onto a two-dimensional surface tangential to the given node;

estimate a two-dimensional electrical conduction velocity vector for the given node based on analysis of the electrophysiological signal for the given node relative to other nodes in the region of interest;

estimate a three-dimensional conduction velocity vector for the given node on the three-dimensional surface of interest based on the two-dimensional electrical conduction velocity vector; and determine a unitary conduction velocity vector field for the given node from the three-dimensional conduction velocity vector.

* * * * *